(12) United States Patent
Stolz et al.

(10) Patent No.: US 7,871,635 B2
(45) Date of Patent: Jan. 18, 2011

(54) USE OF COMPOUND THAT INACTIVATES PROTEIN KINASE A IN A COMPOSITION CONTAINING A COSMETICALLY ACCEPTABLE MEDIUM FOR LIGHTENING THE SKIN

(75) Inventors: Corinne Stolz, Thiais (FR); Christine Garcia, Castres (FR)

(73) Assignee: Societe d'Exploitation de Produits pour les Industries Chimiques SEPPIC, Paris (FR)

( * ) Notice: Subject to any disclaimer, the term of this patent is extended or adjusted under 35 U.S.C. 154(b) by 190 days.

(21) Appl. No.: 12/404,916

(22) Filed: Mar. 16, 2009

(65) Prior Publication Data

US 2009/0175811 A1 Jul. 9, 2009

Related U.S. Application Data

(62) Division of application No. 10/502,627, filed as application No. PCT/FR03/00210 on Jan. 22, 2003, now abandoned.

(30) Foreign Application Priority Data

Jan. 25, 2002 (FR) .................................. 02 00925

(51) Int. Cl.
A61K 31/195 (2006.01)
A61K 7/48 (2006.01)
A61K 7/06 (2006.01)

(52) U.S. Cl. .................................................... 424/401
(58) Field of Classification Search ....................... None
See application file for complete search history.

(56) References Cited

U.S. PATENT DOCUMENTS

| | | | |
|---|---|---|---|
| 5,264,431 A | 11/1993 | Wacker et al. | |
| 5,674,892 A | 10/1997 | Giese et al. | |
| 5,888,482 A | 3/1999 | Amalric et al. | |
| 5,958,431 A | 9/1999 | Brancq et al. | |
| 6,245,821 B1 | 6/2001 | Bulcourt et al. | |
| 6,268,400 B1 | 7/2001 | Amalric et al. | |
| 6,353,034 B1 | 3/2002 | Amalric et al. | |
| 6,488,946 B1 | 12/2002 | Milius et al. | |
| 6,667,396 B2 | 12/2003 | Milius et al. | |
| 2001/0002257 A1 | 5/2001 | Stolz | |

FOREIGN PATENT DOCUMENTS

| | | | |
|---|---|---|---|
| FR | 2 668 080 A1 | 4/1992 | |
| FR | 2 734 496 A1 | 11/1996 | |
| FR | 2 756 195 A1 | 5/1998 | |
| FR | 2 762 317 A1 | 10/1998 | |
| FR | 2 784 680 A2 | 4/2000 | |
| FR | 2 784 904 A1 | 4/2000 | |
| FR | 2 790 977 A1 | 9/2000 | |
| FR | 2 804 432 A1 | 8/2001 | |
| FR | 2 807 435 A1 | 10/2001 | |
| WO | WO 98 09611 A1 | 3/1998 | |
| WO | WO 98 22207 A1 | 5/1998 | |
| WO | WO 99 04757 A1 | 2/1999 | |
| WO | WO 01 57054 A1 | 8/2001 | |

OTHER PUBLICATIONS

Database Caplus; Chemical Abstracts Service, Columbus, Ohio, US; retrieved from STN Database accession No. 1994:563706; and JP 06 157284, Adobansuto Suin Risaachi Kenk, Jun. 3, 1994.
Database Caplus; Chemical Abstracts Service, Columbus, Ohio, US; retrieved from STN Database accession No. 1996:271458; Chemical Abstracts, vol. 124, No. 24, Jun. 10, 1996, Columbus, Ohio, US, abstract No. 325007; and JP 08 053332, Kao Corp.
Database Caplus; Chemical Abstracts Service, Columbus, Ohio, Us; retrieved from STN Database accession No. 2002:1441174; and JP 2002 167319, Asahi Kasei Corp., Jun. 11, 2002.
Database Caplus; Chemical Abstracts Service, Columbus, Ohio, US; retrieved from STN Database accession No. 1975:1031494; and JP 49 093521, Morinaga Milk Industry Co., Ltd., Sep. 5, 1974.
R. Busca, et al: Pigment Cell Res, vol. 13, No. 2, 2000, pp. 60-69.
M.E. Hadley, et al: Annals of the New York Academy of Sciences, vol. 680, 1993, pp. 424-439.
A. Leydet, et al: J. Med. Chem., vol. 39, No. 8, 1996, pp. 1626-1634.
Cosmetic Directive 76/768/EEC amended appendix VII, Dec. 21, 2006.
Siegrist W., Oestreicher M., Stutz M., Girard J. and Eberle A.E.; J. Recep. Res., 8, 1988, 323-343.
Salamon Y., Londos C. and Rodbell M.; Anal. Biochem., 58, 1974, 541-548.
Chijiwa T., Mishima A., Hagiwara M., Sano M., Hayashi K., Inoue T., Naito K., Shioka T., Hidaka H.; J. Biol. Chem., 265, 1990, 5267-5272.
Bradford M.; Anal. Biochem., 72, 1976, 248-254.
Ozeki H., Ito S., Wakamatsu K., Hirobe T., J. Invest. Dermatol., 105, 1995, 361-366.
International Search Report for PCT/FR03/00210, Jun. 30, 2003.

*Primary Examiner*—Humera N Sheikh
*Assistant Examiner*—Jeffrey T Palenik
(74) *Attorney, Agent, or Firm*—Young & Thompson

(57) ABSTRACT

A method of using a compound to lighten the skin by inactivating protein kinase A. The compound may be in a composition with either a pharmacologically or cosmetically acceptable medium. Depending upon the medium and concentration of the compound, the composition may be used either therapeutically or non-therapeutically.

15 Claims, No Drawings

USE OF COMPOUND THAT INACTIVATES PROTEIN KINASE A IN A COMPOSITION CONTAINING A COSMETICALLY ACCEPTABLE MEDIUM FOR LIGHTENING THE SKIN

This application is a divisional application of Ser. No. 10/502,627, filed Jul. 20, 2004, currently pending, which claims priority to PCT/FR03/00210, filed Jan. 22, 2003, which claims priority to French Application No. FR02/00925, filed Jan. 25, 2002. The entire contents of each of the above-identified applications are hereby incorporated by reference.

BACKGROUND

The present invention relates to a novel use of cosmetic active agents for lightening the skin.

Most of the commercially available depigmenting cosmetic formulations are based on kojic acid, arbutin or magnesium ascorbyl phosphate.

The inventors became interested in the development of novel depigmenting active agents that have better compatibility with the skin than those of the prior art. They demonstrated that molecules that inactivate protein kinase A give rise to a skin depigmentation that was attributed hitherto only to inhibition of the enzyme phosphorylated tyrosinase.

SUMMARY

Accordingly, according to a first aspect, the subject of the invention is the use of a compound that inactivates protein kinase A in a composition containing a cosmetically acceptable medium, for lightening the skin.

DESCRIPTION OF PREFERRED EMBODIMENTS

The subject of the invention is the use of a compound that inactivates protein kinase A in a composition containing a cosmetically acceptable medium for lightening the skin.

The relationship between the skin-lightening activity and the inactivation of protein A (PKA) may be explained by following biochemical mechanism:

The inhibition of protein kinase A induces reduced activation of tyrosinase, as a result of the reduced conversion of the latter enzyme into phosphorylated tyrosinase; this reduced activation of tyrosinase results in a reduction in melanin synthesis, giving rise to skin depigmentation.

The expression "compound that inactivates protein kinase A" especially denotes any compound which by incubating protein kinase A in the presence of adenosine triphosphate and a protein that may be phosphorylated, for instance the histone H1, inhibits its phosphorylation, with a percentage of inhibition of greater than or equal to 10%, more particularly with a percentage of inhibition of greater than or equal to 25% and preferably greater than or equal to 50%.

A subject of the invention is, more particularly, the use of a compound of formula (I):

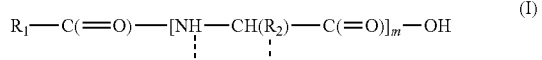
(I)

or salts thereof, in which $R_1$ represents the characterizing chain of a saturated or unsaturated, linear or branched fatty acid containing from 3 to 30 carbon atoms, $R_2$ represents the characterizing chain of an amino acid and m is between 1 and 50, or a mixture of said compounds of formula (I) or salts thereof, in a composition containing a cosmetically acceptable medium, for lightening the skin.

The compound of formula (I) as defined above may be in free acid form or in partially or totally salified form. When the compound of formula (I) is in salified form, the salts are especially alkali metal salts such as the sodium, potassium or lithium salts, alkaline-earth metal salts such as the calcium, magnesium or strontium salts; the ammonium salt or the salt of an amino alcohol, for instance the (2-hydroxyethyl)-ammonium salt. They may also be metal salts such as divalent zinc or manganese salts or trivalent iron, lanthanum, cerium or aluminum salts.

In the description hereinbelow, the expression compound of formula (I) means the compound of formula (I) in free form or in partially or totally salified form.

The expression "characterizing chain" used to define the radicals $R_1$ and $R_2$ denotes the nonfunctional main chain of the fatty acid or of the amino acid under consideration.

Thus, for a fatty acid corresponding to the general formula $R_1$—C(=O)—OH, the characterizing chain will be the chain represented by $R_1$.

The subject of the invention is, mainly, the use of a compound of formula (I) as defined above, in which the group $R_1$—C(=O)— contains from 7 to 22 carbon atoms.

$R_1$—C(=O)— especially represents an octanoyl, decanoyl, undecylenoyl dodecanoyl, tetradecanoyl, hexadecanoyl, octadecanoyl, eicosanoyl, docosanoyl, 8-octadecenoyl, eicosenoyl, 13-docosenoyl, 9,12-octadecadienoyl or 9,12,15-octadecatrienoyl radical.

A subject of the invention is, more particularly, the use of a compound of formula (I) as defined above, in which the fragment $R_1$—C(=O) is chosen from octanoyl, ω-undecylenoyl, dodecanoyl, hexadecanoyl, 8-octa-decenoyl, 13-docosenoyl, 9,12-octadecadienoyl and 9,12,15-octadecatrienoyl radicals.

For an amino acid represented by the general formula (a):

(a)

And for a cyclic amino acid represented by formula (b):

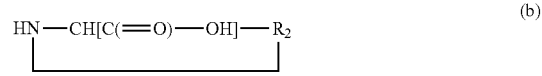
(b)

the characterizing chain will be the chain represented by $R_2$.

$R_2$ especially represents the characterizing chain of an amino acid chosen from glycine, alanine, serine, aspartic acid, glutamic acid, valine, threonine, arginine, lysine, proline leucine, phenylalanine, isoleucine, histidine, tyrosine, tryptophan, asparagine, glutamine, cysteine, cystine, methionine, hydroxyproline, hydroxylysine, sarcosine and ornithine.

The subject of the invention is, mainly, the use of a compound of formula (I) as defined above, in which, in at least one of the residues

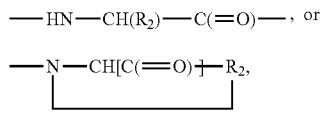

$R_2$ represents the characterizing chain of phenyl-alanine, tyrosine, histidine, methionine, cysteine or tryptophan.

A subject of the invention is more particularly, the use of a compound of formula (I) as defined above, in which m is a decimal number between 1 and 10 and is preferably less than 5.

According to a most particular aspect of the present invention, in formula (I) as defined above, m is less than or equal to 2 and is more particularly less than or equal to 1.4.

According another most particular aspect of the present invention, in formula (I) as defined above, m is equal to 1.

According to another particular variant of the present invention, only one compound of formula (I), as defined above, is used in the composition containing the cosmetically acceptable medium.

According to another particular variant of the present invention, a mixture of compounds of formula (I) as defined above is used, and more particularly
- either a mixture of compounds of formula (I) all comprising the same fragment $R_1$—C(=O),
- or a mixture of compounds of formula (I) in which m is equal to 1 and all comprising the same fragment

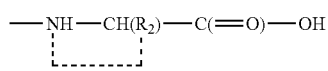

The compounds of formula (I) are generally obtained by N-acylation of compounds of formula (IIIa) or (IIIb) as defined above, or salts thereof.

When it is a mixture of compounds of formula (I), it is obtained, for example, by N-acylation of the amino acid mixture resulting from the total or partial hydrolysis of proteins of any origin.

These proteins may be of animal origin, for instance collagen, elastin, fish flesh protein, fish gelatin, keratin or casein, of plant origin, for instance, proteins from cereals, flowers or fruit, for instance proteins derived from soybean, sunflower, oat, wheat, maize, barley, potato, lupin, bean, sweet almond, kiwi, mango or apple; they may also be proteins obtained from chorellae (unicellular algae), pink algae, yeasts or silk.

This hydrolysis is performed, for example, by heating a protein placed in an acidic or alkaline medium to temperatures of between 60 and 130° C.

This hydrolysis may also be performed enzymatically with a protease, optionally coupled to an alkaline or acidic posthydrolysis. When m is greater than 1, $R_2$ represents one and the same chain or several chains characterizing different amino acids, depending on the protein hydrolyzed and the degree of hydrolysis.

The aminograms of a few proteins of plant origin are given in the following table:

TABLE A

| | Origin of the protein (amino acid proportions expressed as weight %) | | | |
|---|---|---|---|---|
| | Oat | Soybean | Wheat | Sunflower |
| Glycine | 6.9 | 4.2 | 3.2 | 6.2 |
| Alanine | 5.9 | 4.2 | 2.6 | 4.8 |
| Serine | 5.6 | 5.1 | 1.7 | 5.1 |
| Aspartic acid | 16.2 | 11.7 | 3.4 | 10.6 |
| Glutamic acid | 28.3 | 19.1 | 37.9 | 23.6 |
| Valine | 2.9 | 5.0 | 4.2 | 4.8 |
| Threonine | 3.1 | 3.9 | 2.7 | 4.4 |
| Arginine | 6.6 | 7.8 | 3.7 | 8.4 |
| Lysine | 3.6 | 6.2 | 1.9 | 3.2 |
| Proline | 4.7 | 5.4 | 11.7 | 3.0 |
| Leucine | 6.4 | 8.1 | 7.1 | 6.4 |
| Phenylalanine | 1.4 | 5.0 | 5.4 | 4.3 |
| Isoleucine | 2.2 | 4.8 | 3.7 | 4.1 |
| Histidine | 1.7 | 2.6 | 2.4 | 2.0 |
| Tyrosine | 1.5 | 3.5 | 3.1 | 2.7 |
| Methionine | 1.2 | 1.2 | 1.6 | 1.8 |
| Cysteine/cystine | 1.9 | 1.5 | 1.9 | 1.9 |
| Tryptophan | — | 1.0 | 1.0 | 1.3 |
| | Lupin | Potato | Bean | Maize |
| Glycine | 0.9 | 4.8 | 4.0 | 2.4 |
| Alanine | 2.4 | 5.0 | 4.0 | 7.95 |
| Serine | 6.1 | 5.8 | 4.9 | 5.1 |
| Aspartic acid | 15.8 | 12.5 | 10.5 | 10.6 |
| Glutamic acid | 8.0 | 11.5 | 16.8 | 23.6 |
| Valine | 7.9 | 17.1 | 4.5 | 4.8 |
| Threonine | 8.1 | 6.1 | 3.6 | 4.4 |
| Arginine | 16.1 | 5.0 | 9.21 | 8.4 |
| Lysine | 7.1 | 7.8 | 6.5 | 6.2 |
| Proline | — | 5.1 | 4.4 | 3.0 |
| Leucine | 7.45 | 10.4 | 7.4 | 8.1 |
| Phenylalanine | 8.6 | 6.4 | 4.4 | 4.3 |
| Isoleucine | 8.7 | 6.1 | 3.9 | 4.1 |
| Histidine | — | 2.2 | 2.6 | 2.0 |
| Tyrosine | — | 5.7 | 3.6 | 2.7 |
| Methionine | 0.6 | 2.4 | 0.8 | 1.8 |
| Cysteine/cystine | — | 1.6 | 1.7 | 1.9 |
| Tryptophan | 1.2 | 1.4 | 1.2 | 1.3 |
| Ornithine | 0.4 | — | — | — |

The acylation reaction is known to those skilled in the art. It is described, for example, in the international patent application published under the number WO 98/09611. It is performed either on an amino acid or on an amino acid mixture. The acylating agent generally consists of an activated derivative of a carboxylic acid of formula $R_1C(=O)$—OH, such as a symmetrical anhydride of this acid or an acid halide, for instance the acid chloride or acid bromide. It may also consist of a mixture of activated derivatives of carboxylic acids derived from natural oils or fats of animal or plant origin, such as coconut oil, palm kernel oil, palm oil, soybean oil, rapeseed oil, maize oil, beef tallow, spermaceti oil or herring oil.

A subject of the invention is also a nontherapeutic process for treating the skin to lighten it, characterized in that a composition containing a cosmetically acceptable medium and an effective amount of at least one compound that inactivates protein kinase A is applied thereto.

A subject of the invention is also a pharmaceutical composition for performing a therapeutic skin treatment to lighten it, characterized in that it contains a pharmaceutically acceptable medium and an effective amount of at least one compound that inactivates protein kinase A.

In the compositions defined above, the compound that inactivates protein kinase A is generally used in an amount of between 0.01% and 10% of their weight, more particularly between 0.1% and 5% of their weight and most particularly between 1% and 5% of their weight.

According to another particular aspect, a subject of the invention is the use as defined above, characterized in that the compound that inactivates protein kinase A also inactivates adenylate cyclase.

The relationship between the skin-lightening activity and the inactivation of adenylate cyclase may be explained by the following biochemical mechanism:

The inactivation of adenylate cyclase results in reduced conversion of intracellular ATP into cyclic AMP; the reduction in the level of cyclic AMP results in inhibition of protein kinase A (PKA); the inhibition of protein kinase A induces reduced activation of tyrosinase as a result of the reduced conversion of said enzyme into phosphorylated tyrosinase; this reduced activation of tyrosinase results in a reduction in melanin synthesis, giving rise to the skin depigmentation.

The expression "compound that inactivates adenylate cyclase" especially denotes, in the context of the present invention, any compound which, by incubation of this enzyme in the presence of adenosine triphosphate, inhibits its conversion into cyclic adenosine mono-phosphate, with a percentage of inhibition of greater than or equal to 10%, more particularly with a percentage of inhibition of greater than or equal to 25% and preferably greater than or equal to 50%.

The compounds that inactivate adenylate cyclase contained in said composition are more particularly chosen from the compounds of formula (I) as defined above or salts thereof, and most particularly from the compounds of formula (I) as defined above in which $R_1$—C($=$O) is chosen from octanoyl and ω-undecylenoyl radicals and in which, in at least one of the residues

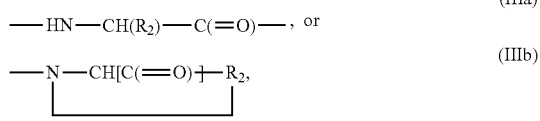

$R_2$ represents the characterizing chain of phenylalanine.

A subject of the invention is also a process as defined above, characterized in that a composition containing a cosmetically acceptable medium and an effective amount of at least one compound that inactivates protein kinase A and adenylate cyclase, and also a pharmaceutical composition as defined above, characterized in that it contains an effective amount of at least one compound that inactivates protein kinase A and adenylate cyclase, are applied to the skin.

According to another particular aspect, a subject of the invention is the use as defined above, characterized in that the compound that inactivates protein kinase A and adenylate cyclase is a compound with affinity for the melanocyte specific hormone (α-MSH) receptor.

The relationship between the skin-lightening activity and the affinity for the α-MSH receptor may be explained by the following biochemical mechanism:

The competition between the hormone α-MSH and the molecule with affinity for the α-MSH receptor results in a reduced level of binding of said hormone to the cell receptors; the consequence of this competition is to inhibit the activity of adenylate cyclase, which results in reduced conversion of intracellular ATP into cyclic AMP; the reduction in the level of cyclic AMP results in inhibition of the enzyme protein kinase A (PKA); the inhibition of protein kinase A induces reduced activation of tyrosinase as a result of the reduced conversion of said enzyme into phosphorylated tyrosinase; this reduced activation of tyrosinase results in a decrease in melanin synthesis, giving rise to skin depigmentation. It is this set of successive inhibitions that bears witness to the α-MSH-antagonist nature of the compounds of the invention.

The expression "compound with affinity for the melanocyte specific hormone, α-MSH, receptor", in the context of the present invention, denotes any compound which displaces the specific binding of a radioactive ligand, for instance nucleoside diphosphate-α-melanocyte specific hormone ([$^{125}$]NDP-α-MSH) to the α-melanocyte specific hormone (α-MSH) type 1 receptor, known as the MC1R receptor, with a percentage of inhibition of greater than or equal to 10%, more particularly with a percentage of inhibition of greater than or equal to 25% and preferably greater than or equal to 50%.

The melanocyte specific hormone antagonists contained in said composition are more particularly chosen from the compounds of formula (I) as defined above, or salts thereof.

A subject of the invention is also a process as defined above, characterized in that a composition containing a cosmetically acceptable medium and an effective amount of at least one compound that inactivates protein kinase A and adenylate cyclase, which is a melanocyte specific hormone antagonist, and also a pharmaceutical composition as defined above, characterized in that at contains an effective amount of at least one compound that inactivates protein kinase A and adenylate cyclase, which is a melanocyte specific hormone antagonist, are applied to the skin.

As shown by the following examples, the compounds used in the cosmetic or therapeutic treatments defined above are characterized, unexpectedly, by skin-lightening activity that is higher than that of the compositions of the prior art. They are thus generally suitable for treatments for lightening the skin, especially by depigmentation, and more particularly for removing or attenuating colored marks appearing on elderly skin.

The compositions used in said treatments are generally in the form of dilute aqueous or aqueous-alcoholic solutions, in the form of simple or multiple emulsions, such as water-in-oil (W/O), oil-in-water (O/W) or water-in-oil-in-water (W/O/W) emulsions, in which the oil is of plant or mineral nature, or in the form of powder. They may also be dispersed or impregnated onto fabric or nonwoven materials, whether they are wipes, paper towels or clothing.

The compositions used in said treatments are administered to the individual in the conventional forms used in cosmetics and pharmacy; these are more particularly topical, oral or parenteral administrations.

In general, the compounds of formula (I) that inactivate protein kinase A, possibly adenylate cyclase and possibly melanocyte specific hormone antagonists, which are used in the invention that is the subject of the present patent application, as defined above, are combined with numerous types of adjuvants or active principles used in cosmetic formulations, whether they are fatty substances, organic solvents, thickeners, gelling agents, softeners, antioxidants, opacifiers, stabilizers, foaming agents, fragrances, ionic or nonionic emulsifiers, fillers, sequestering agents, chelating agents, preserving agents, chemical screening agents or mineral screening agents, essential oils, dyestuffs, pigments, hydrophilic or lipophilic active agents, humectants, for instance glycerol, preserving agents, dyes, fragrances, cosmetic active agents, mineral or organic sunscreens, mineral fillers, for instance iron oxides, titanium oxides and talc, synthetic fillers, for instance Nylons and crosslinked or noncrosslinked poly(m- ethyl methacrylate), silicone elastomers, sericites or plant extracts, or alternatively lipid vesicles, or any other ingredient usually used in cosmetics.

As examples of oils that may be combined with the compound of formula (I), mention may be made of paraffins, isoparaffins, white mineral oils, plant oils, animal oils, synthetic oils, silicone oils and fluoro oils; and more particularly:

oils of plant origin, such as sweet almond oil, coconut oil, castor oil, jojoba oil, olive oil, rapeseed oil, groundnut oil, sunflower oil, wheatgerm oil, maize germ oil, soybean oil, cottonseed oil, alfalfa oil, poppy oil, pumpkin oil, evening primrose oil, millet oil, barley oil, rye oil, safflower oil, candlenut oil, passionflower oil, hazelnut oil, palm oil, shea butter, apricot kernel oil, beauty-leaf oil, sysymbrium oil, avocado oil or calendula oil;

ethoxylated plant oils;

oils of animal origin, such as squalene or squalane;

mineral oils, such as liquid paraffin, liquid petroleum jelly and isoparaffins;

synthetic oils, especially fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate, isocetyl lanolate, fatty acid monoglycerides, diglycerides and triglycerides, for instance glyceryl triheptanoate, alkylbenzoates, poly-α-olefins, polyolefins, for instance polyisobutene, synthetic isoalkanes, for instance isohexadecane or isododecane, perfluoro oils and silicone oils. Among the silicone oils, mention may be made more particularly of dimethylpolysiloxanes, methylphenylpolysiloxanes, silicones modified with amines, silicones modified with fatty acids, silicones modified with alcohols, silicones modified with alcohols and fatty acids, silicones modified with polyether groups, modified epoxy silicones, silicones modified with fluoro groups, cyclic silicones and silicones modified with alkyl groups.

As other fatty materials that may be combined with this active agent, mention may be made of fatty alcohols or fatty acids.

Among the thickening and/or emulsifying polymers used in the present invention, there are, for example, homopolymers or copolymers of acrylic acid or of acrylic acid derivatives, acrylamide homopolymers or copolymers, homopolymers or copolymers derived from acrylamide, homopolymers or copolymers of acrylamidomethylpropanesulfonic acid, of vinyl monomer or of trimethylaminoethyl acrylate chloride, sold under the names Carbopol™, Utltrez™ 10, Permulen™ TR1, Permulen™ TR2, Simulgel™ A, Simulgel™ NS, Simulgel™ EPG, Simulgel™ EG, Luvgel™ EM, Salcare™ SC91, Salcare™ SC92, Salcare™ SC95, Salcare™ SC96, Flocare™ ET100, Hispagel™, Sepigel™ 305, Sepigel™ 50, Sepigel™ 502, Flocare™ ET58 and Stabileze™ 06; hydrocolloids of plant or biosynthetic origin, for instance xanthan gum, karaya gum, carrageenates or alginates; silicates; cellulose and its derivatives; starch and its hydrophilic derivatives; polyurethanes.

Among the waxes that may be used in the context of the present invention, examples that may be mentioned include beeswax; carnauba wax; candelilla wax; ouricury wax; Japan wax; cork fiber wax or sugarcane wax; paraffin waxes; lignite waxes; microcrystalline waxes; lanolin wax; ozokerite; polyethylene wax; hydrogenated oils; silicone oils; plant waxes; fatty alcohols and fatty acids that are solid at room temperature; glycerides that are solid at room temperature.

Among the emulsifiers that may be used in the context of the present invention, examples that may be mentioned include fatty acids; ethoxylated fatty acids; fatty acid esters of sorbitol; ethoxylated fatty acid esters; polysorbates; polyglycerol esters; ethoxylated fatty alcohols; sucrose esters; alkylpolyglycosides; sulfated and phosphated fatty alcohols or mixtures of alkylpolyglycosides and of fatty alcohols described in French patent applications 2 668 080, 2 734 496, 2 756 195, 1 762 317, 2 784 680, 2 784 904, 2 791 565, 2 790 977, 2 807 435 and 2 804 432.

As examples of active principles that may be combined with the compound of formula (I) in order to synergistically potentiate its properties, mention may be made of compounds with lightening or depigmenting activity, for instance arbutin, kojic acid, hydroquinone, ellagic acid, vitamin C, magnesium ascorbyl phosphate, polyphenol extracts, grape extracts, pine extracts, wine extracts, olive extracts, pond extracts, N-acyl proteins, N-acyl peptides, N-acylamino acids, partial hydrolyzates of N-acyl proteins, amino acids, peptides, total protein hydrolyzates, partial protein hydrolyzates, polyols (for instance glycerol, butylene glycol, etch, urea, pyrrolidonecarboxylic acid or derivatives of this acid, glycyrrhetinic acid, α-bisabolol, sugars or sugar derivatives, poly-saccharides or derivatives thereof, hydroxy acids, for instance lactic acid, vitamins, vitamin derivatives, for instance retinol, vitamin E and its derivatives, minerals, enzymes, coenzymes, for instance coenzyme Q10, hormones or 'hormone-like' substances, soybean extracts, for instance Raffermine™, wheat extracts, for instance Tensine™ or Gliadine™, plant extracts, such as tannin-rich extracts, isoflavone-rich extracts or terpene-rich extracts, extracts of freshwater or seawater algae, essential waxes, bacterial extracts, minerals, lipids in general, lipids such as ceramides or phospholipids, active agents with slimming activity, for instance caffeine or its derivatives, active agents with antimicrobial activity or with purifying action on greasy skin, such as Lipacide™ PVB, active agents with an energizing or stimulatory property, for instance Sepitonic™ M3 or Physlogényl™, panthenol and its derivatives, for instance Sepicap™ MP, antiaging active agents, for instance Sepilift™ DPHP, Lipacide™ PVB, Sepivinol™ or Sepivital™, moisturizing active agents, for instance Sepicalm™ S, Sepicalm™ VG and Lipacide™ DPHP, "anti-photoaging" anti aging active agents, active agents for protecting the integrity of the dermo-epidermal junction, and active agents for increasing the synthesis of components of the extra-cellular matrix.

As sunscreens that may be incorporated into the composition according to the invention, mention may be made of any of those featured in the Cosmetic Directive 76/768/EEC amended appendix VII.

According to a final aspect of the present invention, a subject thereof is N-(ω-undecylenoyl)phenylalanine of formula:

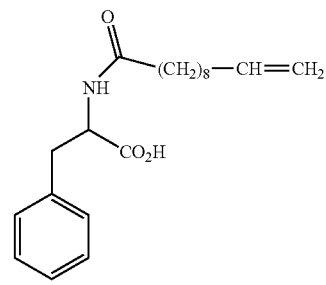

its cosmetic use, pharmaceutical compositions containing it and emulsions characterized in that they have a content thereof of between 0.01% and 10% of their weight, more particularly between 0.1% and 5% of their weight and most particularly between 1% and 5% of their weight.

The experimental study that follows illustrates the invention without, however, limiting it.

EXAMPLES

In Vitro Evaluation of the Depigmenting Activity of Undecylenoylphenylalanine The object or this study was to demonstrate the depigmenting activity of N-undecylenoylphenylalanine, according to a mechanism involving the antagonist effect of the molecule on the α-melanocyte specific hormone (α-MSH) type 1 receptor, known as the MC1R receptor. This type of pharmacological receptor is mainly found in the melanocytes.

The result of melanogenesis using this receptor is shown. It especially involves adenylate cyclase, cAMP, protein kinase A and tyrosinase. By binding to the receptor MC1R, α-MSH stimulates the α subunit of the stimulating protein G (Prot GaS). This protein activates the enzyme adenylate cyclase, which converts adenosine triphosphate (ATP) into cyclic adenosine monophosphate (cAMP). The cAMP activates the A protein kinases (PKA), which convert tyrosinase into phosphorylated tyrosinase, which stimulates melanogenesis.

In a first step, the study thus consisted in evaluating the binding capacities of N-undecylenoylphenylalanine to the receptors MC1R, found in the melanocytes.

In a second step, the effect of N-undecylenoylphenylalanine on the activities of adenylate cyclase, protein kinase A and tyrosinase was evaluated.

In a third step, the depigmenting activity of N-undecylenoylphenylalanine on melanocyte cultures of the B16/F1 line was determined in vitro by measuring the intracellular and extracellular melanin contents and by measuring the tyrosinase activity.

In a fourth step, the depigmenting activity of N-undecylenoylphenylalanine was evaluated in a model of pigmented reconstructed human epidermides (photo-type IV) in order to test the efficacy of the product under real application conditions (topical application of the formulated product).

The effects of the product were compared with those observed in the case of various reference depigmenting products, hydroquinone, kojic acid and arbutin.

1—Affinity Study on MC1R Receptors

The affinity of N-undecylenoylphenylalanine, kojic acid and arbutin was compared.

MC1R receptors are isolated from cell membranes of mouse melanocytes of the B16/F1 line via the method described in: Siegrist W., Oestreicher M., Stutz M., Girard J. and Eberle A. E.; J. Recep. Res., 8, 1988, 323-343".

N-Undecylenoylphenylalanine, arbutin and kojic acid are diluted to a concentration of 10 mg/ml in decinormal aqueous sodium hydroxide solution. They are each tested separately at concentrations of 0.1 mg/ml and 1 mg/ml. Sodium hydroxide has no effect on the parameter studied.

The MC1R receptors are incubated, in the presence or absence of these products, with an iodine-125 labeled radioactive ligand, the nucleoside diphosphate-α-melanocyte specific hormone [$^{125}$I]NDP-α-MSH at a concentration of 0.05 nM, for 90 minutes at 22° C.

Control cultures are incubated, in the absence of product, and in the presence of the radioactive ligand. Each test is performed in triplicate.

After incubation for 90 minutes, the cell membranes are rapidly filtered and the filters are washed several times with cold buffer. The amount of radioactive ligand bound to the MC1R receptors is measured using a scintillation counter (Topcount, Packard).

The results given in the table below are the means of the three tests performed for each of the products. They are expressed as a percentage of specific binding relative to the control group and as a percentage of inhibition of this binding.

| Test products | Activity relative to the control | | Inhibition of specific binding by the test products | |
|---|---|---|---|---|
| | at 0.1 mg/ml | at 1 mg/ml | at 0.1 mg/ml | at 1 mg/ml |
| Arbutin | 100.80 ± 0.55 | 96.30 ± 4.16 | 0% | 3.7% |
| Kojic acid | 104.50 ± 1.38 | 124.00 ± 1.87 | 0% | 0% |
| N-Undecylenoylphenylalanine | 57.70 ± 2.38 | 4.20 ± 0.86 | 42.3% | 95.8% |

The results demonstrate that at the test concentrations, neither arbutin nor kojic acid, which are the reference depigmenting compounds, displaces the specific binding of the ligand, [$^{125}$I]NDP-α-MSH; in contrast, N-undecylenoylphenylalanine displaces 42% and 96%, respectively, of the binding of [$^{125}$I]NDP-α-MSH to the MC1R receptors.

2—Study of Adenylate Cyclase Activation

The influence of N-undecylenoylphenylalanine, kojic acid and arbutin on the conversion of ATP into cAMP was compared via a radioimmunological assay.

Adenylate cyclase, which converts ATP into cAMP, is extracted from rat brains via the method described in "Salamon Y., Londos C. and Rodbell M.; Anal. Biochem., 58, 1974, 541-548"; it is then activated with 10 μM of forskolin.

N-Undecylenoylphenylalanine, arbutin and kojic acid are diluted to a concentration of 10 mg/ml in decinormal aqueous sodium hydroxide solution. They are each tested separately at a concentration of 1 mg/ml. Sodium hydroxide has no effect on the parameter studied.

The activated enzyme is incubated, in the presence or absence of these products, and in the presence of 0.5 mM of ATP, for 30 minutes at 30° C.

Control cultures are incubated, in the absence of product, and in the presence of ATP. Each test is performed in triplicate.

After incubation for 30 minutes, the amount of cAMP produced is evaluated via a radioimmunological assay performed using a commercial kit; the radioactivity is measured with a scintillation counter (Topcount, Packard), a small radioactivity count reflecting small activation of adenylate cyclase.

The results given in the table below are the means of the three tests performed for each of the products. They are expressed as a percentage of enzymatic activity relative to the control group and as a percentage of inhibition.

| Test products | Enzymatic activity relative to the control | Inhibition of adenylate cyclase activity |
|---|---|---|
| Arbutin | 109.7 ± 4.6% | 0% |
| Kojic acid | 45.0 ± 6.5% | 55% |
| N-Undecylenoylphenylalanine | −16.0 ± 0.5% | 100% |

The results demonstrate that at 1 mg/ml, whereas arbutin has no effect on this enzyme, kojic acid induces a moderate effect and N-undecylenoylphenylalanine induces total inactivation.

3—Study of Protein Kinase A Activity

The influence of N-undecylenoylphenylalanine, kojic acid and arbutin on the phosphorylation of tyrosinase with protein kinase A (PK A) was compared.

Protein kinase A is extracted from bovine brains via the method described in: "Chijiwa T., Mishima A., Hagiwara M., Sano M., Hayashi K., Inoue T., Naito K., Shioka T., Hidaka H.; J. Biol. Chem., 265, 1990, 5267-5272". It is then activated with 3 µM of cAMP.

N-Undecylenoylphenylalanine, arbutin and kojic acid are diluted to a concentration of 10 mg/ml in decinormal aqueous sodium hydroxide solution. They are each tested separately at a concentration of 1 mg/ml. Sodium hydroxide has no effect on the parameter studied.

The activated enzyme is incubated, in the presence or absence of these products, and in the presence of $^{33}$P-labeled radioactive ATP ($[\gamma\text{-}^{33}P]ATP$) and 200 µg/ml of histone $H_1$, for 20 minutes at 30° C.

Control cultures are incubated, in the absence of product, and in the presence of radioactive ATP and histone $H_1$. Each test is performed in triplicate.

After incubation for 20 minutes, the amount of $^{33}$P-labeled phosphorylated histone $H_1$ is measured using a scintillation counter (Topcount, Packard), a small radioactivity count reflecting small activation of the protein kinase A.

The results given in the table below are the means of the three tests performed for each of the products. They are expressed as a percentage of enzymatic activity relative to the control group and as a percentage of inhibition.

| Test products | Enzymatic activity relative to the control | Inhibition of protein kinase A activity |
|---|---|---|
| Arbutin | 90.9 ± 8.4% | 9.1% |
| Kojic acid | 113.3 ± 5.0% | 0% |
| N-Undecylenoyl-phenylalanine | −0.4 ± 0.3% | 100% |

The results demonstrate that at 1 mg/ml, N-undecylenoylphenylalanine totally inhibits the protein kinase A activity, in contrast to kojic acid or arbutin.

4—Study of Phosphorylated Tyrosinase Activity

The influence of N-undecylenoylphenylalanine, hydroquinone, kojic acid and arbutin on the activity of phosphorylated tyrosinase was compared by measuring the conversion of L-tyrosine into L-dopa and dopaquinone, which is a colored product that can be quantified via spectrophotometry (at 490 nm).

The tyrosinase used is a commercial product extracted from fungi.

N-Undecylenoylphenylalanine, hydroquinone, arbutin and kojic acid are diluted to a concentration of 10 mg/ml in decinormal aqueous sodium hydroxide solution. They are each tested separately at concentrations of 0.1 mg/ml and 1 mg/ml. Sodium hydroxide has no effect on the parameter studied.

Tyrosinase at 66.66 IU/ml is incubated, in the presence or absence of these products, and in the presence of 0.2 mM of tyrosine, for 10 minutes at 37° C.

Control cultures are incubated, in the absence of product, and in the presence of tyrosinase and L-tyrosine. Each test is performed in triplicate.

After incubation for 10 minutes, the amount of dopaquinone histone formed is measured using a spectrophotometer at 490 nm.

The results given in the table below are the means of the three tests performed for each of the products.

They are expressed as IU/l of tyrosinase activity and as a percentage of inhibition of the enzymatic activity relative to the control.

| Test products | Percentage of inhibition of tyrosinase activity with the test products relative to the control | |
|---|---|---|
| | at 0.1 mg/ml | at 1 mg/ml |
| Hydroquinone | 78 | 80 |
| Arbutin | 73 | 80 |
| Kojic acid | 76 | 80 |
| N-Undecylenoylphenylalanine | 80 | 100 |

The results demonstrate that at concentrations of 0.1 mg/ml and 1 mg/ml, all the test products significantly inhibit the activity of tyrosinase. However, the inhibitory activity of undecylenoylphenylalanine is greater than that of the other test products.

5—Study of the Depigmenting Activity in B16/F1 Melanocyte Cultures

The influence of N-undecylenoylphenylalanine, hydroquinone, kojic acid and arbutin on the production of intracellular melanin and extracellular melanin, in B16/F1 melanocyte cultures and on the activity of phosphorylated tyrosinase, was compared.

Mouse melanocytes of the B16/F1 line are inoculated in 96-well culture plates at a density of 1500 cells/well. The cells are cultured in a culture medium (MCM medium) at 37° C. under a humid atmosphere containing 5% $CO_2$. The cells are used at 60% of confluence, i.e. 4 days after inoculation.

The MCM medium has the following composition: DMEM medium (Dulbecco's Modified Eagle's Medium) containing 4.5 g/l of glucose supplemented with L-glutamine (2 mM), penicillin (50 IU/ml), streptomycin (50 µg/ml) and fetal calf serum (10% v/v).

N-Undecylenoylphenylalanine is diluted to 4 mg/ml in decinormal aqueous sodium hydroxide solution. It is tested at 40 µg/ml in the MCM medium. Sodium hydroxide has no effect on the parameters analyzed.

Hydroquinone is tested at 5 µg/ml in the MCM medium. Given its toxicity, it is not tested at 40 µg/ml.

Arbutin and kojic acid are tested at 40 µg/ml in the MCM medium.

The melanocyte cultures are incubated in the presence of the test product or of the reference products for 72 hours at 37° C., under a humid atmosphere containing 5% $CO_2$.

Control cultures are incubated, in the absence of product, in the MCM medium. These control cultures are prepared on each culture plate.

Each test is performed six times.

5.1—Measurement of the Extracellular Melanin Content

After incubation for 72 hours, the incubation media of the cells (n=6) are taken up and stored at −80° C. until the time of evaluation of the effects. The extracellular melanin is quantified by spectrophotometry at 450 nm. A melanin calibration range is prepared in parallel.

The results are expressed as µg/ml of extracellular melanin and as a percentage of inhibition relative to the control group.

| Test products | Extracellular melanin (control: 43 ± 11 µg/ml) | Inhibition of extracellular melanin production |
|---|---|---|
| Hydroquinone at 5 µg/ml | 7 ± 1 µg/ml | 85% |
| Arbutin at 40 µg/ml | 23 ± 6 µg/ml | 47% |
| Kojic acid at 40 µg/ml | 13 ± 2 µg/ml | 70% |
| N-Undecylenoylphenylalanine at 40 µg/ml | 12 ± 1 µg/ml | 72% |

5.2—Measurement of the Intracellular Melanin Content

After incubation for 72 hours, a portion of the cell carpet (n=3) is rinsed with phosphate-buffered saline (PBS; pH=7.4), the composition of which is as follows: NaCl: 8 g/l, $Na_2HPO_4$: 1.15 g/l; $KH_2PO_4$: 0.2 g/l; KCl: 0.2 g/l; $CaCl_2$: 0.1 g/l; $MgCl_2$: 0.1 g/l. The intracellular melanin is solubilized by incubation, with stirring, for 30 minutes at room temperature in the presence of decanormal sodium hydroxide.

The intracellular melanin is quantified by spectrophotometry at 450 nm. A melanin calibration range is prepared in parallel.

The results are expressed as µg/ml of intracellular melanin and as a percentage of inhibition relative to the control group.

| Test products | Intracellular melanin obtained (control: 20 ± 4 µg/ml) | Inhibition of intracellular melanin production |
|---|---|---|
| Hydroquinone at 5 µg/ml | 0.2 ± 0.1 µg/ml | 100% |
| Arbutin at 40 µg/ml | 16 ± 2 µg/ml | 19% |
| Kojic acid at 40 µg/ml | 17 ± 1 µg/ml | 17% |
| N-Undecylenoylphenylalanine at 40 µg/ml | 7 ± 3 µg/ml | 66% |

5.3—Measurement of the Phosphorylated Tyrosinase Activity

After incubation for 72 hours, the second portion of the cell carpet (n=3) is rinsed with PBS. The cells are lyzed with Triton™ X100 at a concentration of 0.1% (w/v) for 30 minutes at room temperature. The activity of the endogenous tyrosinase is evaluated by adding 0.1% (w/v) of L-dopa, followed by incubation for 3 hours at 37° C. in the absence of air and light. The dopaquinone formed by the reaction between the tyrosinase and the L-dopa is measured by spectrophotometry at 450 nm. A calibration range of purified tyrosinase is prepared in parallel.

The results are expressed as IU/ml of tyrosinase activity and as a percentage of inhibition relative to the control group.

| Test products | Tyrosinase activity (control: 9.8 ± 0.3 IU/ml) | Inhibition of tyrosinase activity |
|---|---|---|
| Hydroquinone at 5 µg/ml | 3.0 ± 0.3 IU/ml | 69% |
| Arbutin at 40 µg/ml | 7.6 ± 1.1 IU/ml | 23% |
| Kojic acid at 40 µg/ml | 6.8 ± 0.1 IU/ml | 31% |
| N-Undecylenoylphenylalanine at 40 µg/ml | 3.2 ± 0.6 IU/ml | 67% |

5.4—Measurement of the Intracellular Protein Content

This assay allows the cytotoxicity of the test products to be evaluated. It is performed in cell lysates prepared as described in the preceding paragraph.

The protein assay is performed according to the Coomassie blue method described by: "Bradford M.; Anal. Biochem., 72, 1976, 248-254". The measurement is performed by spectrophotometry at 640 nm. A bovine serum albumin (BSA) calibration range is prepared in parallel.

The results are expressed as mg/ml of proteins and as a percentage of inhibition relative to the control group.

| Test products | Total proteins (control: 0.45 ± 0.01) | Inhibition of protein quantity |
|---|---|---|
| Hydroquinone a 5 µg/ml | 0.28 ± 0.01 mg/ml | 38% |
| Arbutin at 40 µg/ml | 0.43 ± 0.01 mg/ml | 5% |
| Kojic acid at 40 µg/ml | 0.41 ± 0.02 mg/ml | 10% |
| N-Undecylenoylphenylalanine at 40 µg/ml | 0.38 ± 0.01 mg/ml | 17% |

5.5—Results Analysis

After incubation for 72 hours, hydroquinone, tested at 5 µg/ml, inhibits the extracellular melanin content by 85%, the intracellular melanin content by 100% and the tyrosinase activity by 69%, respectively. However, the depigmenting effect of hydroquinone is partly derived from its cytotoxic effect, since a 38% decrease in the total protein quantity is observed.

Arbutin, tested at 40 µg/ml, inhibits the extracellular melanin content by 47%, the intracellular melanin content by 19% and the tyrosinase activity by 23%, respectively. At this concentration, arbutin has no effect on the total protein content.

Kojic acid, tested at 40 µg/ml, inhibits the extracellular melanin content by 70%, the intracellular melanin content by 17% and the tyrosinase activity by 31%, respectively. At this concentration, kojic acid has no significant effect on the total protein content.

N-Undecylenoylphenylalanine, tested at 40 µg/ml, inhibits the extracellular melanin content by 72%, the intracellular melanin content by 66% and the tyrosinase, activity by 67%, respectively. At this concentration, N-undecylenoylphenylalanine decreases the total protein content by 17%.

N-Undecylenoylphenylalanine thus has depigmenting activity, demonstrated by a concomitant reduction of the intracellular and extracellular melanin contents and of tyrosinase activity. Unlike that of hydroquinone, its depigmenting activity is not linked to a cytotoxic effect. It has higher depigmenting activity than arbutin and kojic acid.

6—Study of the Depigmenting Activity in Reconstructed Human Epidermides

The influence of N-undecylenoylphenylalanine, hydroquinone, kojic acid and arbutin on the production of intracellular melanin and extracellular melanin, in B16/F1 melanocyte cultures and on the staining of epidermides, was compared.

Pigmented human epidermides (phototype IV) supplied by Skinethic, of 0.63 cm$^2$, are reconstructed from a coculture of normal human keratinocytes (skin of the forearm, 3 year old donor, 2nd passage) and from normal human melanocytes (skin of the forearm, 4 year old donor of phototype IV, 3rd passage). The keratinocyte/melanocyte ratio is 10:1. The cocultures are inoculated onto inert polycarbonate filters. They are cultured for 10 days in the medium supplied by Skinethic, consisting of MCDB 153 medium supplemented with 5 µg/ml of insulin, 1.5 mM of calcium and growth factors.

For these tests, the products are tested after having been incorporated into a cosmetic formulation consisting of an emulsion comprising an aqueous phase, 10% by weight of a fatty phase (Lanol™ 1688), 2% by weight of an emulsifier (Simugel™ EG), 0.5% by weight of preserving agents (0.3% of Sepicide™ HB+0.2% of Sepicide™ CI). After incorporation of the active principle, the formulation is adjusted to pH=5.5.

N-Undecylenoylphenylalanine, arbutin and kojic acid are incorporated therein at elevated temperature (75° C.), in a proportion of 1% or 3% by weight per unit volume (w/v).

On account of its toxicity, hydroquinone is incorporated therein at a concentration of 0.1% by weight per unit volume (w/v).

The epidermides are cultured in 6-well plates containing 1 ml of the medium described above. They are incubated at 37° C. under a humid atmosphere containing 5% $CO_2$.

The formulations containing the various active principles are applied to the surface of the epidermides, at a rate of 2 µl/epidermis, using a sterile bacteriological inoculator. The application is performed every day for 4 consecutive days. The incubation medium of the reconstructed epidermides is renewed every day for 4 consecutive days.

Control epidermides are treated with a formulation free of active principle. Each test is performed in duplicate.

6.1—Chromametric Measurement of the Epidermal Pigmentation

Three days after the final topical application, the color of the epidermides is evaluated using a chromameter (Minolta) by measuring the following parameters L*, a* and b*:

L* is the lightness index. A depigmenting product should increase this parameter;

a* represents the color spectrum from blue to green. A depigmenting product should reduce this parameter;

b*: represents the color spectrum from red to yellow. A depigmenting product should reduce this parameter.

The results are expressed in arbitrary units (AU) of each parameter and as a percentage of the control group.

| Test products | L*<br>Control:<br>41.38 ± 0.69 AU | | a*<br>Control:<br>10.23 ± 0.51 AU | | b*<br>Control:<br>7.54 ± 0.00 AU | |
| --- | --- | --- | --- | --- | --- | --- |
| | AU | % | AU | % | AU | % |
| Hydroquinone formulated at 0.1% (w/v) | 40.59 ± 2.41 | −9 | 10.19 ± 1.21 | 0 | 7.73 ± 0.03 | +3 |
| Arbutin formulated at 1% (w/v) | 40.48 ± 0.85 | +2 | 10.02 ± 0.13 | −2 | 7.64 ± 0.19 | +1 |
| Arbutin formulated at 3% (w/v) | 41.13 ± 0.54 | +1 | 9.86 ± 0.18 | −4 | 7.73 ± 0.34 | +3 |
| Kojic acid formulated at 1% (w/v) | 40.11 ± 1.41 | +3 | 10.90 ± 0.51 | +7 | 7.67 ± 0.03 | +3 |
| Kojic acaid formulated at 3% (w/v) | 41.69 ± 0.65 | 0 | 9.36 ± 1.02 | −8 | 7.13 ± 0.09 | −5 |
| N-Undecylenoyl-phenylalanine formulated at 1% (w/v) | 41.34 ± 1.15 | 0 | 9.01 ± 1.33 | −12 | 5.96 ± 0.42 | −21 |
| N-Undecylenoyl-phenylalanine formulated at 3% (w/v) | 45.228 ± 1.49 | +9 | 8.78 ± 0.52 | −14 | 5.38 ± 0.06 | −29 |

6.2—Measurement of the Intracellular Melanin Content

Three days after the final topical application and after the chromametric measurement, the intracellular melanin is extracted from the epidermides by incubation for 45 minutes at 100° C. in Soluene™ 350 (200 µl/epidermis), as described in "Ozeki H., Ito S., Wakamatsu K., Hirobe T.; J. Invests. Dermatol., 105, 1995, 361-366. The samples are centrifuged for 10 minutes at 10 000 rpm.

The extracted intracellular melamin is measured by spectrophotometry at 500 nm. A melanin calibration range is prepared in parallel.

The results are expressed as mg/ml of intracellular melanin and as a percentage of inhibition relative to the control group.

| Test products | Intracellular melanin (control: 347 ± 2 μg/ml) | Inhibition of the amount of intracellular melanin |
|---|---|---|
| Hydroquinone formulated at 0.1% (w/v) | 317 ± 0 μg/ml | −9% |
| Arbutin formulated at 1% (w/v) | 242 ± 46 μg/ml | −28% |
| Arbutin formulated at 3% (w/v) | 263 ± 16 μg/ml | −24% |
| Kojic acid formulated at 1% (w/v) | 273 ± 2 μg/ml | −21% |
| Kojic acid formulated at 3% (w/v) | 234 ± 19 μg/ml | −33% |
| N-Undecylenoyl-phenylalanine formulated at 1% (w/v) | 264 ± 9 μg/ml | −24% |
| N-Undecylenoyl-phenylalanine formulated at 3% (w/v) | 264 ± 11 μg/ml | −24% |

6.3—Results Analysis

Hydroquinone, tested in topical application at a concentration of 0.1% (w/v) in an emulsion, has no significant effect either on the chromametric parameters L*, a* and b* or on the melanin content of the reconstructed human epidermides. The absence of a depigmenting effect of hydroquinone is due either to the low test concentration, which was deliberately selected as noncytotoxic, or to the short duration of the treatment.

Arbutin, tested in topical application at 1% and 3% (w/v) in an emulsion, has no significant effect on the chromametric parameters L*, a* and b*. However, it inhibits the melanin content of the reconstructed human epidermides by 28% and 24%, respectively.

Kojic acid, tested in topical application at 1% and 3% (w/v) in an emulsion, has no significant effect on the chromametric parameters L*, a* and b*. However, in inhibits the melanin content of the reconstructed human epidermides by 21% and 33%, respectively.

N-Undecylenoylphenylalanine, tested in topical application at 1% (w/v) in an emulsion, inhibits the b* color parameter by 15% and the melanin content of the reconstructed human epidermides by 24%.

At a concentration of 3% (w/v), N-undecylenoylphenylalanine increases the L* parameter by 9% and concomitantly reduces the a* color parameter by 14%, the b* color parameter by 29% and the melanin content of the reconstructed epidermides by 24%.

These tests on reconstructed epidermides show that N-Undecylenoylphenylalanine has improved depigmenting activity compared with that of the reference products, insofar as it has an influence both on the chromametric parameters and on the intracellular melanin contents.

7—Conclusion

The results obtained in this study together demonstrate strong depigmenting activity of N-undecylenoylphenylalanine. This activity is quantified both in melanocyte cultures and in a 3D model composed of reconstructed human epidermides. In contrast to the reference products, the depigmenting activity of T-undecylenoylphenylalanine involves the MC1R receptors. N-Undecylenoylphenylalanine is an MC1R receptor antagonist and inhibits all the steps of the α-MSH cycle involved in melanogenesis.

Cosmetic Formulation Examples

Example 2

Lightening Care Emulsion for Mature Skin

| | |
|---|---|
| Montanov ™ 202 | 02.00% |
| Montanov ™ 63 | 02.00% |
| Caprylic capric triglycerides | 10.00% |
| Squalane | 10.00% |
| Water | q.s. 100% |
| N-Undecylenoylphenylalanine | 01.00% |
| Sepigel ™ 305 | 00.70% |
| Magnesium ascorbyl phosphate | 02.00% |
| Sepicide ™ HB | 00.30% |
| Sepicide ™ CI | 00.20% |
| Fragrance | 00.50% |

Example 3

Lightening Firming Care Emulsion

| | |
|---|---|
| Montanov ™ 202 | 03.00% |
| 24% sodium hydroxide | 00.06% |
| Ethylhexyl methoxycinnamate | 06.00% |
| Lanol ™ 1688 | 08.00% |
| Benzophenone-3 | 04.00% |
| Water | q.s. 100% |
| N-Undecylenoylphenylalanine | 02.00% |
| Simulgel ™ NS | 00.50% |
| Sepilift ™ DPHP | 00.50% |
| Dimethicone | 02.00% |
| Cyclomethicone | 02.00% |
| Arbutin | 0.3% |
| Sepicide ™ HB | 00.30% |
| Sepicide ™ CI | 00.20% |
| Fragrance | 00.10% |

Example 4

Lightening Cream-Gel Containing α-Hydroxy Acids

| | |
|---|---|
| Hydroxyethylcellulose | 00.80% |
| Ethylhexyl octanoate | 05.00% |
| 60% sodium lactate | 14.00% |
| Water | q.s. 100% |
| N-Undecylenoylphenylalanine | 03.00% |
| Sepigel ™ 305 | 04.20% |
| Sepicide ™ HB | 02.00% |
| Sepicide ™ CI | 03.00% |
| Fragrance | 00.10% |

Example 5

Lightening Care Emulsion

| | |
|---|---|
| Montanov ™ L | 01.00% |
| Cetyl alcohol | 02.00% |
| Isodecyl neopentanoate | 12.00% |
| Cetaryl octanoate | 10.00% |
| Glycerol | 03.00% |
| Water | q.s. 100% |
| N-Undecylenoylphenylalanine | 01.00% |
| Simugel ™ EG | 02.00% |
| Kojic acid | 01.00% |
| Sepicide ™ HB | 00.30% |
| Sepicide ™ CI | 00.20% |
| Fragrance | 00.10% |

Example 6

Lightening Lotion

| | |
|---|---|
| Oramix ™ CG110 | 05.00% |
| Kathon ™ CG | 00.08% |
| Water | q.s. 100% |
| N-Undecylenoylphenylalanine | 01.00% |
| Fragrance | 00.10% |

This lotion may be sold in bottles or impregnated into wipes.

The definitions of the commercial products used in the examples are as follows:

Sepilift™ DHP (INCI name: dipalmitoyl hydroxyproline), sold by the company SEPPIC.

Sepicide™ HB is a preserving mixture comprising phenoxyethanol, methyl paraben, ethyl paraben, propyl paraben and butyl paraben, sold by the company SEPPIC.

Sepicide™ CI is imidazolidinylurea, sold by the company SEPPIC.

Sepicalm™ VG (INCI name: sodium palmitoyl proline and extract of water lily flower (sold by the company SEPPIC.

Kathon™ CG (INCI name: methylisothiazolinone/methylchloroisothiazolinone).

Simulgel™ EG is a copolymer inverse latex (INCI name: sodium acrylate/sodium acryloyldimethyltaurate copolymer and isohexadecane and Polysorbate 80) sold by the company SEPPIC.

Simulgel™ NS is a copolymer inverse latex (INCI name: hydroxyethyl acrylate/sodium acryloyldimethyltaurate copolymer and squalane and Polysorbate 60) sold by the company SEPPIC.

Lanol™ 1688 is cetearyl ethylhexanoate, sold by the company SEPPIC.

Sepigel™ 305 is a polymer inverse latex (INCI name, polyacrylamide and C13-C14 isoparaffin and Laureth 7).

Montanov™ L is an emulsifier based on C14-C22 alcohol and on C12-C20 alkyl polyglucoside.

Montanov™ 68 is an emulsifier based on cetearyl alcohol and cetearyl polyglucoside.

Montanov™ 202 is an emulsifier based on arachidyl alcohol, behenyl alcohol and arachidyl polyglucoside.

It will be understood that many additional changes in the details and which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method of lightening skin comprising inactivating protein kinase A with a composition comprising:
    a) a cosmetically acceptable medium; and
    b) a compound N-(ω-undecylenoyl) phenylalanine of formula (Ia):

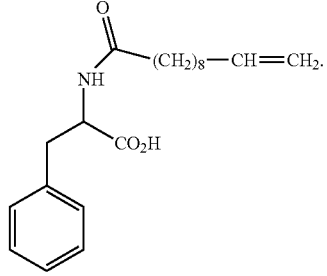

2. The method of claim 1, wherein said N-(ω-undecylenoyl) phenylalanine of formula (Ia) also inactivates adenylate cyclase.

3. A method of lightening skin comprising inactivating protein kinase A with a composition comprising:
    a) a cosmetically acceptable medium; and
    b) a compound of general formula (I):

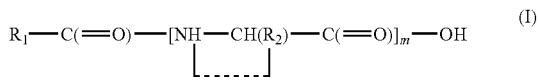

or salts thereof, wherein:
1) said $R_2$—C(=O)— is a radical of general formula (II):

$R_1$—C(=O)—         (II), and $R_1$ represents the characterizing chain of a fatty acid comprising:
   i) about 3 to about 30 carbon atoms; and
   ii) a characteristic comprising at least one member selected from the group consisting of:
       aa) saturated;
       bb) unsaturated;
       cc) linear; and
       dd) branched;
2) said

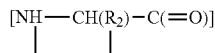

is a residue comprising at least one member selected from the group consisting of:
a) a residue of general formula (IIIa)

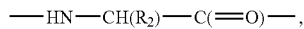 (IIIa)

and
b) a residue of general formula (IIIb)

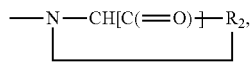 (IIIb)

and
$R_2$ represents the characterizing chain of an amino acid; and
3) m is between about 1 and about 50.

4. The method of claim 3, wherein said radical $R_1$ comprises about 7 to about 22 carbon atoms.

5. The method of claim 4, wherein said radical comprises at least one member selected from the group consisting of:
a) octanoyl;
b) decanoyl;
c) undecylenoyl;
d) dodecanoyl;
e) tetradecanoyl;
f) hexadecanoyl;
g) octadecanoyl;
h) eicosanoyl;
i) docosanoyl;
j) 8-octadecenoyl;
k) eicosenoyl;
l) 13-docosenoyl;
m) 9,12-octadecadienoyl; and
n) 9,12,15-octadecatrienoyl radical.

6. The method of claim 5, wherein said radical comprises at least one member selected from the group consisting of:
a) octanoyl;
b) ω-undecylenoyl;
c) dodecanoyl;
d) hexadecanoyl;
e) 8-octadecenoyl;
f) 13-docosenoyl;
g) 9,12-octadecadienoyl; and
h) 9,12,15-octadecatrienoy-l.

7. The method of claim 6, wherein said $R_2$ comprises at least one functional group of an amino acid selected from the group consisting of:
a) glycine;
b) alanine;
c) serine;
d) aspartic acid;
e) glutamic acid;
f) valine;
g) threonine;
h) arginine;
i) lysine;
j) proline;
k) phenylalanine;
l) isoleucine;
m) histidine;
n) tyrosine;
o) tryptophan;
p) asparagine;
q) glutamine;
r) cysteine;
s) cystine;
t) methionine;
u) hydroxyproline;
v) hydroxylysine;
w) sarcosine;
x) ornithine; and
y) leucine.

8. The method of claim 7, wherein said $R_2$ comprises at least one functional group of an amino acid selected from the group consisting of:
a) phenylalanine;
b) tyrosine;
c) histidine;
d) methionine;
e) cysteine; and
f) tryptophan.

9. The method of claim 7, wherein:
a) said radical comprises at least one member selected from the group consisting of:
1) octanoyl radicals; and
2) ω-undecylenoyl radicals; and
b)
wherein said $R_2$ represents the functional group of phenylalanine.

10. The method of claim 8, wherein said m is less than about 5.

11. The method of claim 10, wherein said m is less than or equal to about 2.

12. The method of claim 11, wherein said m is less than or equal to about 1.4.

13. The method of claim 12, wherein said m is equal to about 1.

14. The method of claim 13, wherein said compound further comprises an affinity for the melanocyte specific hormone (α-MSH) receptor.

15. A method of lightening skin comprising inactivating the protein kinase A with a composition comprising:
a) a cosmetically acceptable medium; and
b) a compound N-(ω-undecylenoyl) phenylalanine of formula (Ia):

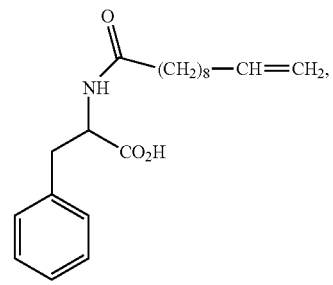 (Ia)

wherein said N-(ω-undecylenoyl) phenylalanine of formula (Ia) inactivates adenylate cyclase and has an affinity for the melocytic specific hormone (α-MSH).

* * * * *